(12) United States Patent
Taagaard et al.

(10) Patent No.: US 6,551,480 B1
(45) Date of Patent: Apr. 22, 2003

(54) REFERENCE ELECTRODE

(75) Inventors: Michael Taagaard, Horsholm (DK); Flemming Aas, Soborg (DK)

(73) Assignee: Radiometer Medical A/S, Bronshoj (DK)

(*) Notice: Subject to any disclaimer, the term of this patent is extended or adjusted under 35 U.S.C. 154(b) by 0 days.

(21) Appl. No.: 09/701,829

(22) PCT Filed: May 27, 1999

(86) PCT No.: PCT/DK99/00283

§ 371 (c)(1),
(2), (4) Date: Feb. 8, 2001

(87) PCT Pub. No.: WO99/63334

PCT Pub. Date: Dec. 9, 1999

(30) Foreign Application Priority Data

Jun. 4, 1998 (DK) .................................. PA 1998 00762

(51) Int. Cl.$^7$ ............................................. G01N 27/401
(52) U.S. Cl. ........................................ 204/435; 204/279
(58) Field of Search ................................ 204/435, 415, 204/279

(56) References Cited

U.S. PATENT DOCUMENTS

| | | | | |
|---|---|---|---|---|
| 3,505,196 A | * | 4/1970 | Dahms | |
| 3,915,829 A | * | 10/1975 | Krebs | |
| 4,166,021 A | * | 8/1979 | Ross et al. | |
| 4,177,126 A | | 12/1979 | Imaki et al. | |
| 4,495,053 A | * | 1/1985 | Souza | |
| 4,544,455 A | * | 10/1985 | Eisenhardt et al. | |
| 5,370,783 A | * | 12/1994 | Carlson et al. | |
| 5,384,031 A | * | 1/1995 | Anderson et al. | |
| 5,516,413 A | * | 5/1996 | Foster et al. | |
| 6,068,744 A | * | 5/2000 | Seto et al. | |

FOREIGN PATENT DOCUMENTS

| | | |
|---|---|---|
| DE | 372404 | 2/1989 |
| JP | 10197474 | 7/1998 |

OTHER PUBLICATIONS

Radiometer, ABL5, Reference Manual, Edition A, Code No. 985–681, Mar. 1994, p. 1.4.1.2.*

* cited by examiner

Primary Examiner—T. Tung
(74) Attorney, Agent, or Firm—Bryan Cave LLP; Maurice B. Stiefel

(57) ABSTRACT

The reference electrode comprises an electrode plug and a chamber (16) closed at the rear containing an electrolyte. The chamber (16) has an aperture (23) covered by a membrane (26) of a material permitting diffusion of ions therethrough, but whose surface is closed for proteins and similar macromolecular substances. A diffusion tight diaphragm element (27) having a through-going orifice (30) located radially within the aperture is situated on the outer side of the ion diffusion membrane (26) relative to the chamber, and the orifice (30) is smaller than the aperture (23).

15 Claims, 2 Drawing Sheets

REFERENCE ELECTRODE

The invention relates to a reference electrode comprising an electrode plug and a chamber closed at the rear containing an electrolyte, the chamber having an aperture covered by a membrane of a material permitting diffusion of ions therethrough, but whose surface is closed for proteins and similar macromolecular substances.

Reference electrodes are used as part of an electrode chain when electrochemically measuring the content of a particular chemical substance (species) in a liquid sample. The reference electrode establishes a constant or stable potential, which in an ideal situation is independent of the composition of the liquid sample, but in practice varies with the so-called liquid junction potential. The liquid junction potential is the potential difference, created across the interface between the sample liquid and electrolyte, and this potential varies with varying dilution and varying ion composition between sample and electrolyte. This variation affects the measuring results which become imprecise or misleading.

When using a reference electrode of the present kind, it is decisive that the concentration of the potential controlling ion in the electrolyte is constant or at least kept within certain limits in order to obtain stability and thus to achieve reliable measurements. It is known to fulfil this requirement either by using a saturated solution as electrolyte, which, however, is not always possible due to practical/technical causes, or by using a system where the electrolyte is renewed after each measurement which, for example, is the case at a so-called open salt bridge system. Without renewal of the electrolyte, the diffusion from the sample to the electrolyte may change the composition of the electrolyte and thus change the reference electrode potential.

A known reference electrode, E111 Reference Electrode sold by the company Radiometer Medical A/S, Åkandevej 21, DK-2700 Brønshøj, Denmark, comprises an electrode plug and a chamber closed at the rear containing a saturated KCl solution. The chamber has an aperture covered by a porous double membrane which permits diffusion of ions therethrough both radially and across the membrane. The porous membrane comprises of a 12 $\mu$m thick polycarbonate layer and a 18 $\mu$m thick cellophane layer. The saturated KCl solution diffuses through the porous membrane which serves as salt bridge, thus establishing contact between the reference electrode and the sample. This known electrode suffers from the drawback that liquids in the measuring chamber pollutes the liquid junction, and thus reduces the use of the electrode.

Figure 1:
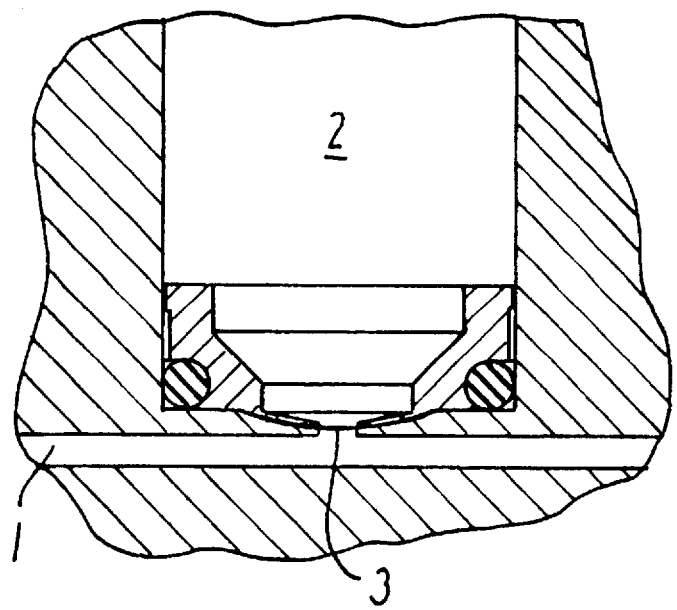

Another known reference electrode is used in an analyser, Chiron 800 series, which is manufactured and sold by the company CHIRON DIAGNOSTICS CORPORATION, Ameryville, Calif., USA. This electrode also comprises a chamber containing an electrolyte and having an aperture covered by a membrane which permits ion diffusion. However, in this electrode the chamber is open at the rear. The following FIG. 1 shows an outline of the area at the aperture and the membrane of this known reference electrode. The membrane is of cellophane and is fixed between two walls having concentric apertures, of which the inner aperture relative to the chamber is approx. 0.7 mm in diameter and the outer aperture is approx. 0.8 mm in diameter.

In the latter electrode there is an actual flow of electrolyte out through the membrane, in reality, the electrode uses an open salt bridge system. This raises the problem that the electrolyte penetrates into the liquid sample being measured, which is polluted and subsequently cannot be used for other measurements. Besides, the use of an open salt bridge system requires that the electrolyte is continuously being supplied.

The purpose of the invention is to provide a reference electrode which compared to the prior art has reduced the exchange of ions between the electrolyte and the sample liquid.

This is achieved by means of a reference electrode comprising an electrode plug and a chamber closed at the rear and containing an electrolyte, the chamber having an aperture covered by a membrane of a material permitting diffusion of ions therethrough, but whose surface is closed for proteins and similar macromolecular substances, and which is characterised in comprising a diffusion tight diaphragm element having a radial through-going orifice situated within the aperture, which diaphragm element is situated on the outer side of the ion diffusion membrane relative to the chamber, and which orifice is equal to or smaller than the aperture, thus limiting variations in the liquid junction potential.

Since the aperture in the chamber is greater than the orifice in the diaphragm element, ions form the electrolyte in the chamber are supplied to the orifice area of the ion diffusion membrane from all directions both axially and radially, whereas ions from the sample liquid may only approach the orifice area of the ion diffusion membrane in an axial direction at the specific area of the orifice. Thus, the diffusion of ions from the electrolyte to the ion diffusion membrane is greater than the diffusion of ions from the sample to the ion diffusion membrane. Therefore, ions from the sample liquid do not pollute the electrolyte by diffusing into the electrode chamber and the electrolyte remains present in full concentration in the chamber. As a result, it is not necessary to supply further electrolyte to the chamber during the life time of the electrode.

Theoretically, the reference electrode should operate satisfactorily having almost the same orifice size in the diaphragm element as the aperture, but according to tests made by the inventors, the diaphragm element should preferably cover at least 80–90% and preferably at least approx. 93% of the area of the aperture, corresponding to the area of the orifice being max. 10–20% and preferably max. 7% of the area of the aperture, and/or the orifice should preferably have a diameter of max. 0.4 mm, more preferably max. 0.25 mm.

A reduction of the size of the orifice relative to the size of the aperture improves the radial supply of ions from the chamber to the orifice through the ion diffusion membrane.

A reduction of the absolute size of the orifice reduces the exchange of ions between the electrolyte and the sample liquid, resulting in only an insignificant change in the concentration of ions in the electrolyte and in particular of the potential determining ion during use.

The diameter of the orifice should be as small as possible when measuring pure liquids without dissolved macromolecular compounds. However, when measuring for example blood or another liquid containing proteins or other macromolecular substances the diameter should not be so small that there may be a risk of wholly or partly clogging. Therefore, the diameter of the orifice is preferably greater than 0.05 mm.

In a preferred embodiment, the orifice has a diameter in the area of approx. 0.12–0.25 mm, and a nominal diameter of 0.18 mm.

The diaphragm element preferably is a membrane in order to achieve a small thickness of the element, thereby avoiding that special diffusion conditions in the orifice arises, which may affect the potential. The thickness of the element to be used depends on the size of the orifice. The orifice diameter of the diaphragm may be adjusted depending on the character of the sample liquid, as relatively large orifice diameters are used (larger than approx. 0.05 mm) when measuring sample media having protein content such as blood. The thickness of the diaphragm membrane is preferably in the interval 5–25 µm. The ratio between the orifice diameter and the membrane thickness of the diaphragm is preferably within the interval 0.008–100. In a preferred embodiment the diaphragm membrane is of polyester and the ratio between the orifice diameter and the thickness of the diaphragm membrane is 12 (0.18 mm/15 µm).

In a further preferred embodiment, the diaphragm element is made of polyester, but it may be made of any material which is tight against the used electrolyte and the occurring sample liquids, and which may be processed as required by the actual manufacturing method of the reference electrode, including the preparation of an orifice in it.

Further, from DE-A-37 24 040 is known a membrane unit (membrankörper) for a membrane covered measuring electrode (a modified Clark-electrode) for measuring oxygen concentration in a fluid. The active surface of the membrane unit is limited by a diaphragm comprising an orifice which lies over the measuring electrode and preferably has a smaller diameter than this. The measuring electrode includes a chamber containing an electrolyte, and a membrane being impenetrable to the fluid and the electrolyte, but oxygen penetrable is stretched across the chamber. The orifice diaphragm limits the diffusion of oxygen from the fluid to the measuring electrode and side diffusion is excluded. This design ensures stabile and reproducible oxygen measurements. Thus, DE-A-37 24 040 relates to a substantially different electrode with a substantially different problem than the present electrode.

In a preferred embodiment of the reference electrode according to the invention the ion diffusion membrane permits three-dimensional diffusion of ions and is non-repellent for the electrolyte.

When using a water-based electrolyte, it is preferred that the ion diffusion membrane (preferably permitting three-dimensional diffusion) is of cellophane as by the above-mentioned known reference electrodes. However, synthetic or native materials may be used which may contain water in their polymer matrix. In these materials the water is either in direct contact with the polymer chains in a hydrated/swelled state due to polarity and free volume, or is contained in three-dimensionally combined pores or along hydrophilic fibres, which are distributed in the matrix, making tree-dimensional transport, penetration or diffusion of water possible. Mentioned among these materials may be chemical (cross-linked) or physical gels, for example the mentioned cellophane which is hydrophilic, but not water-soluble, cross-linked hydrophilic polymers (hydro gels), fibrous materials such as composites of the kind which are used in drain layers in disposable sanitary articles, cellular plastic (reticular, foaming) and heterogeneous compounds of polymers with mutually penetrating net.

Preferably a porous, mechanically strengthening membrane is located within the ion diffusion membrane. For example, this strengthening membrane may be of polycarbonate and be perforated with a pore diameter of approx. 0.1 µm and a perforation degree of approx. 2.4%.

In a preferred embodiment, the electrolyte is a sodium format solution having a concentration in the area 1–8 M.

By means of the invention, it has been possible to develop a reference electrode consisting of replaceable units or a replaceable plug-in module. The reference electrode according to the invention may be shaped as an independent unit separate from a measuring electrode or constitute part of a unit integrated with a measuring electrode, i. e. be part of a so-called combination electrode.

Figure 2:
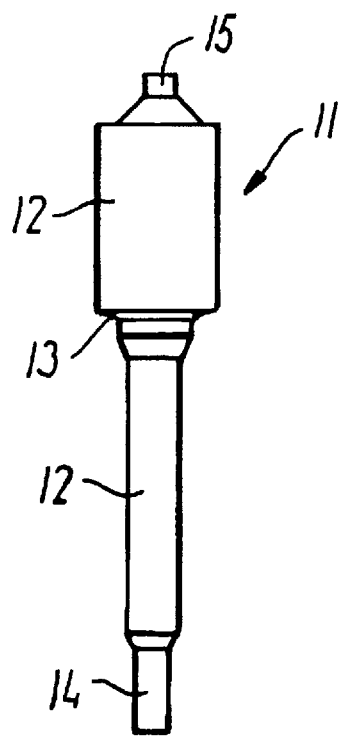
Figure 3:
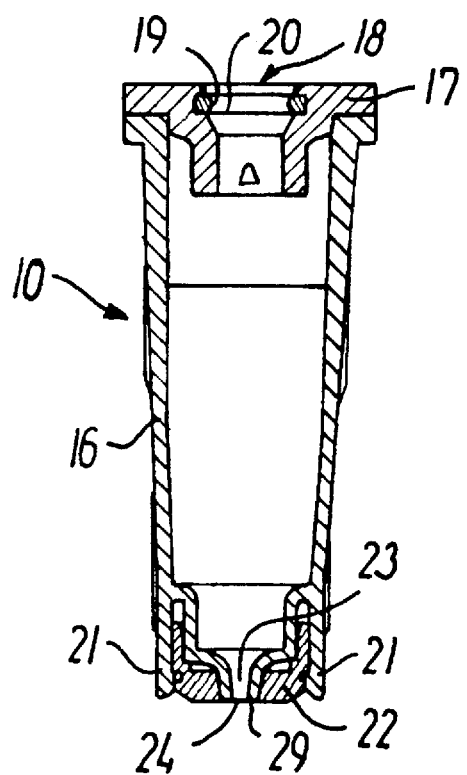
Figure 4:
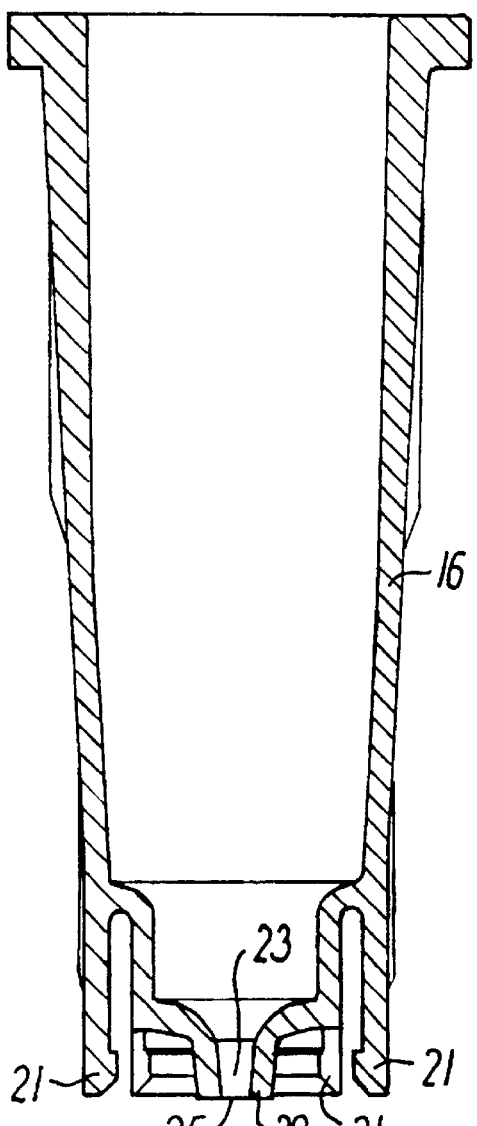
Figure 5:
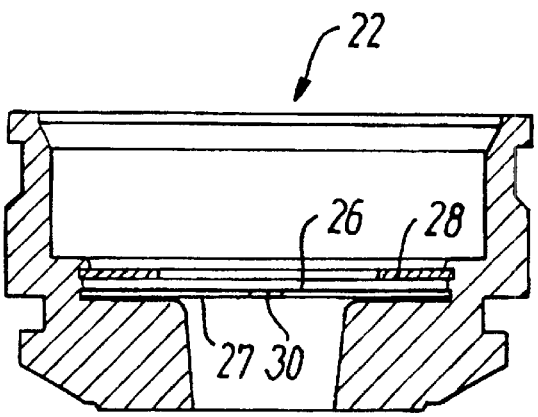
Figure 6:
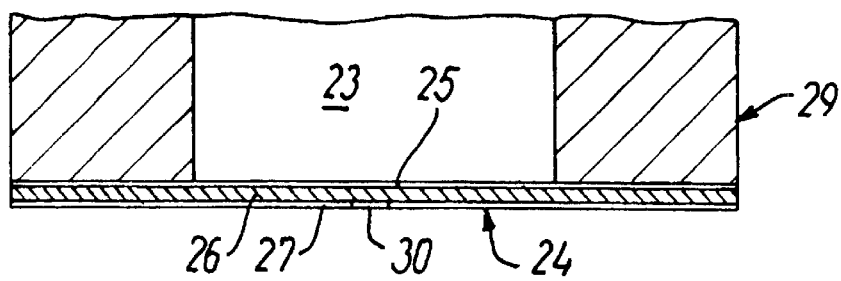

The invention will be further described below with reference to the drawing. In the drawing:

FIG. 1 shows part of a known reference electrode,

FIG. 2 shows an electrode plug of a reference electrode according to the invention, FIG. 3 shows a vertical section through a chamber unit of a reference electrode according to the invention, FIG. 4 shows an enlarged vertical section through a part of the chamber comprising the aperture, FIG. 5 shows an even further enlarged section through a membrane retainer ring to be mounted on the chamber unit, and FIG. 6 shows an enlarged outline of the membrane system according to the invention.

FIG. 1 shows an outline of the front of the above-mentioned known reference electrode, which is manufactured and sold by the company CHIRON DIAGNOSTICS CORPORATION. The electrode comprises a conduit 1 and a chamber 2 containing a salt bridge solution. A sample may be led into the conduit 1. The chamber 2 and the conduit 1 are separated by a cellophane membrane 3 which is stretched across an aperture between the conduit 1 and the chamber 2. At the aperture there is an orifice of ⌀0.07 mm towards the chamber 2 and an orifice of ⌀0.8 mm towards the conduit 1. During use, the chamber 2 continuously has to be refilled with salt bridge solution, as there is an actual flow of salt bridge solution out through the cellophane membrane.

The reference electrode according to the invention comprises a chamber unit 10, shown on FIG. 3, and an electrode plug 11, shown on FIG. 2. The electrode plug 11 comprises of a silver pin embedded in an ABS holder 12 with a seat 13 for an O-ring. One end 14 of the silver pin is chlorinated, while the other end 15 is plated with gold. When mounted in an analyser, the end 15 will engage an electrode contact of the analyser.

The chamber unit 10 comprises a polycarbonate jacket 16, which is closed on the top by means of a polycarbonate guide 17 for the electrode plug 11. The polycarbonate guide 17 has an aperture 18, in which an O-ring 19 is embedded, and which is closed by a rupture foil 20. The chamber unit 10 contains an electrolyte or salt bridge solution which is a sodium formate solution in the present example. However, other electrolytes may be used, for example a KCl-solution.

At the bottom of the polycarbonate jacket 16, a retainer ring 22 is retained by means of snap-lock claws 21, the retainer ring 22 fixing a membrane system 24, which is described below. At its lower end, the polycarbonate jacket 16 has a tip 29 with an aperture 23. The aperture 23 has an inner diameter of ⌀0.9 mm and is closed by the mentioned membrane system 24.

In the shown preferred embodiment, the membrane system 24 comprises a porous polycarbonate membrane 25, a cellophane membrane 26 and a diaphragm membrane 27 of polyester as shown on FIG. 5 and FIG. 6.

The polycarbonate membrane 25 is welded to the end of the polycarbonate jacket 16 across the aperture 23, while the cellophane membrane 26 and the diaphragm membrane 27 are fixed by the retainer ring 22 and an additional lock ring 28, so when assembling, the membranes slide forward and follows the front of the polycarbonate jacket 16.

In the embodiment, the polycarbonate membrane 25 is 12 µm thick and has a pore diameter of 0.1 µm and a porosity of 2.4% ($3 \times 10^8$ pores per $cm^2$). The polycarbonate membrane 25 both functions as a diffusion limiter and provides a mechanical stabilisation of the membrane system 24. Other materials than polycarbonate may be used provided the membrane 25 may be fixed to the polycarbonate jacket 16 by welding or in another appropriate way.

In the embodiment, the cellophane membrane 26 is 18 µm thick and functions i.a. to avoid protein interference. Thus, it works partly as a protein barrier and partly as a distributor layer for the sodium ions and formate ions.

In the embodiment, the diaphragm membrane 27 is 15 µm thick and has an orifice 30 with a diameter in the interval 0.12 mm–0.25 mm.

The lock ring 28 (see FIG. 5) is of acetate film having a thickness of 150 mm. It functions to hold or fix the cellophane membrane 26 and the diaphragm membrane 27 in place in the retainer ring 22 during manufacture of the chamber unit 10.

When mounting the membrane system to the end of the polycarbonate jacket 16, the polycarbonate membrane 25 is first welded at the end of the tip 29. The diaphragm membrane 27, the cellophane membrane 26 and the lock ring are then placed in the retainer ring 22 as shown in FIG. 5, and the retainer ring 22 is pressed up around the tip 29 to the position shown in FIG. 3, where it is secured by the snap-lock claws 21. Thus, the cellophane membrane 26 and the diaphragm membrane 27 will be stretched across the tip 29 and the aperture 23 on the outside of the polycarbonate membrane 25. The membrane system after mounting is shown in FIG. 6.

In the described embodiment, the reference electrode is a replaceable unit, which may be inserted into an analyser. When the reference electrode is to be used, the chlorinated end 14 of the electrode plug 11 is introduced through the polycarbonate guide 17, thus rupturing the rupture foil 20, and is introduced until the O-ring 19 rests in the seat 13. The electrode plug 11 is now sealingly retained by the polycarbonate guide 17, and the reference electrode may be installed in the analyser.

With the membrane system, a very small exchange between the salt bridge solution and the surroundings is achieved. This exchange includes evaporation of water (mainly during storage) and dilution by diffusion of ions to cleaning liquids and sample liquids. Evaporation leads to a rise of the concentration of the salt bridge solution, while dilution leads to a reduction of the concentration. The inventors have experienced that a concentration of sodium formate between 1 M and 8 M is acceptable to the measuring results when measuring for example pH, blood gasses, ions and metabolites in automatic blood analysers, which measure very small sample quantities in the quantity of 30–250 µL in measuring chambers, each having a size of approx. 3–5 µL/measuring chamber. Therefore, when filling the chamber unit, an aqueous sodium formate solution having a concentration of 4 M is used in order to allow fluctuation in both upwards and downwards directions. The chloride concentration in the electrolyte is adjusted to the measuring liquid and is preferably 0.13 M. pH of the electrolyte is preferably adjusted to approx. 5.5 with 12 M HCl.

As mentioned, a certain dilution of the salt bridge solution takes place by exchange with sample liquid or calibration solution, i. e. during use. The inventors have calculated that with the above-mentioned dimensions of the different parts of the membrane system and with a quantity of added salt bridge solution of 0.9 ml, the durability of the reference electrode unit is more than 3 months in blood analysers of the abovementioned type when performing 100 test measurements per day and two different calibration procedures each second and fourth hour respectively.

What is claimed is:

1. A reference electrode for contacting an ion-containing sample comprising an electrode plug and a chamber (16) closed at the rear and containing an ion-containing electrolyte, the chamber (16) having an aperture (23) covered by a membrane (26) of a material permitting diffusion of ions therethrough, but whose surface is closed for proteins and similar macromolecular substances, the reference electrode further comprising a diffusion tight diaphragm membrane (27) being situated on the outer side of the ion diffusion membrane (26) relative to the chamber (16), the diffusion tight diaphragm membrane (27) having a through-going orifice (30) which is located within the aperture (23) and is smaller than the aperture (23), whereby diffusion of ions from the electrolyte to the ion diffusion membrane is greater than diffusion of ions from the sample to the ion diffusion membrane.

2. A reference electrode according to claim 1 characterized in that the diaphragm membrane (27) covers at least 80% of the aperture (23).

3. A reference electrode according to claim 1 characterized in that the orifice (30) has a diameter of up to 0.4 mm.

4. A reference electrode according to claim 1 characterized in that the orifice (30) has a diameter from about 0.12 mm to about 0.25 mm.

5. A reference electrode according to claim 1, characterized in that the diameter of the orifice (30) is larger than 1 µm.

6. A reference electrode according to claim 1 characterized in that the reference electrode is a replaceable unit.

7. A reference electrode according to claim 1 characterized in that a porous, mechanically strengthening membrane (25) backs the ion diffusion membrane (26).

8. A reference electrode according to claim 7 characterized in that the strengthening membrane (25) is made of polycarbonate and is perforated with a pore diameter of approximately 0.1 µm and a perforation degree of approximately 2.4%.

9. A reference electrode according to claim 1 characterized in that the electrolyte is a sodium formate solution with a concentration from about 1 M to about 8 M.

10. A reference electrode according to claim 1 characterized in that the electrolyte has a chloride concentration of about 0.13 M.

11. A reference electrode according to claim 1, characterized in that the pH of the electrolyte is adjusted to pH 5.5.

12. A reference electrode according to claim 1 characterized in that the ratio of the orifice diameter (30) to the thickness of the diaphragm membrane (27) is from 0.0008 to 100.

13. Reference electrode according to claim 12, characterized in that the diaphragm membrane (27) is of polyester and that the ratio between the orifice diameter (30) and the thickness of the diaphragm membrane (27) is 12.

14. A reference electrode according to claim 1 wherein the diaphragm membrane covers at least about 93% of the area of the aperture.

15. A reference electrode according to claim 1 wherein the orifice (30) has a diameter of maximum 0.25 mm.

* * * * *

UNITED STATES PATENT AND TRADEMARK OFFICE
CERTIFICATE OF CORRECTION

PATENT NO.     : 6,551,480 B1
DATED          : April 22, 2003
INVENTOR(S)    : Michael Taagaard and Flemming Aas It is certified that error appears in the above-identified patent and that said Letters Patent is hereby corrected as shown below:

Column 6,
Line 25, after "the" please insert -- area of --.

Signed and Sealed this

Sixteenth Day of September, 2003

JAMES E. ROGAN
*Director of the United States Patent and Trademark Office*